United States Patent
Staniszewska et al.

(10) Patent No.: US 11,536,651 B2
(45) Date of Patent: Dec. 27, 2022

(54) DEVICE FOR DETECTING AND/OR DETERMINING THE CONCENTRATION OF AN ANALYTE PRESENT IN A TISSUE AND A METHOD AND USE OF THIS DEVICE

(71) Applicant: SDS OPTIC sp. Z o.o., Lublin (PL)

(72) Inventors: Magdalena Staniszewska, Motycz (PL); Marcin Staniszewski, Motycz (PL)

(73) Assignee: SDS OPTIC S.A., Lublin (PL)

( * ) Notice: Subject to any disclaimer, the term of this patent is extended or adjusted under 35 U.S.C. 154(b) by 722 days.

(21) Appl. No.: 16/477,877

(22) PCT Filed: May 26, 2017

(86) PCT No.: PCT/PL2017/050030
§ 371 (c)(1),
(2) Date: Jul. 13, 2019

(87) PCT Pub. No.: WO2018/132022
PCT Pub. Date: Jul. 19, 2018

(65) Prior Publication Data
US 2021/0063307 A1      Mar. 4, 2021

(30) Foreign Application Priority Data

Jan. 14, 2017   (PL) .......................... 420189

(51) Int. Cl.
*G01N 21/45*      (2006.01)
*A61B 5/00*       (2006.01)
(Continued)

(52) U.S. Cl.
CPC ............. *G01N 21/45* (2013.01); *A61B 5/444* (2013.01); *A61M 5/32* (2013.01); *G01N 21/77* (2013.01);
(Continued)

(58) Field of Classification Search
CPC ... A61B 5/444; A61M 5/32; G01N 2021/458; G01N 2021/7779; G01N 2021/7796; G01N 21/45; G01N 21/77
See application file for complete search history.

(56) References Cited

U.S. PATENT DOCUMENTS

| 2004/0018635 A1 | 9/2004 | Beaudoin et al. |
| 2010/0063493 A1 | 3/2010 | Anastasie |

(Continued)

FOREIGN PATENT DOCUMENTS

| CN | 101032390 A | 9/2007 |
| CN | 105526883 A | 8/2012 |

(Continued)

*Primary Examiner* — Mark R Gaworecki
(74) *Attorney, Agent, or Firm* — Craft Chu PLLC; Andrew W. Chu

(57) ABSTRACT

The device for detecting and/or determining the concentration of an analyte present in a tissue includes a sensor which is an optical fibre interferometer, and one interferometer arm being coated with an immobilised binding agent enabling selective binding of the analyte. The interferometer arm is mounted inside a guide enabling puncturing the tissue and performing an in situ measurement without the necessity to collect or prepare a sample. The guide is provided with a closed guide face, longitudinal perforations on sidewalls enabling the analyte to reach the binding agent, and an opening in the input end of the guide for introducing the interferometer with the arm into the guide. At the input end, the opening is sealed, enabling the isolation of the interior of the guide from the surroundings. The interferometer is mounted in a position in which the interferometer does not touch the inside walls of the guide.

13 Claims, 8 Drawing Sheets

(51) Int. Cl.
*A61M 5/32* (2006.01)
*G01N 21/77* (2006.01)

(52) U.S. Cl.
CPC .............. *G01N 2021/458* (2013.01); *G01N 2021/7779* (2013.01); *G01N 2021/7796* (2013.01)

(56) References Cited

U.S. PATENT DOCUMENTS

| | | | |
|---|---|---|---|
| 2011/0136132 A1* | 6/2011 | Tseng | A61B 5/14546 435/7.1 |
| 2012/0116234 A1 | 5/2012 | Farcy et al. | |
| 2012/0194661 A1 | 8/2012 | Lee et al. | |

FOREIGN PATENT DOCUMENTS

| | | |
|---|---|---|
| JP | 2005249696 A | 9/2005 |
| WO | 2004066824 A2 | 8/2004 |
| WO | 2004102170 A1 | 11/2004 |

\* cited by examiner

DEVICE FOR DETECTING AND/OR DETERMINING THE CONCENTRATION OF AN ANALYTE PRESENT IN A TISSUE AND A METHOD AND USE OF THIS DEVICE

CROSS-REFERENCE TO RELATED APPLICATIONS

See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The object of the invention is a device for detecting of and/or quantitative determination of an analyte present in tissue, comprising a sensor, which is an optical fibre interferometer, and also a method for detecting and/or quantitative determination of an analyte present in tissue by means of this device and use of this device for detecting and/or quantitative determination of an analyte present in tissue.

2. Description of Related Art Including Information Disclosed Under 37 CFR 1.97 and 37 CFR 1.98

In state of the art, a device for detection of toxins in milk samples based on a biosensor has been described, wherein the surface of a Fabry-Perot-type interferometer, being a glass microplate with capillary flow has been coated with fragments of antibodies, the so-called Fab' (Chalyan T et al., Asymmetric Mach-Zehnder Interferometer Based Biosensors for Aflatoxin M1 Detection, Biosensors 2016, 6, 1; doi:10.3390/bios6010001).

The application U.S. Ser. No. 10/483,586 (publication no. US20040186359 A) describes a diagnostic device using detection by means of a coated optical fibre; which nonetheless requires implanting in the body.

The document Clinical Chemistry, 1991, Evaluation of the Fiber-Optic Antibody-Based Fluoroimmunosensor for DNA Adducts in Human Placenta Samples, T. Vo-Dinh, J. P. Alarie, R. W. Johnson, M. J. Sepaniak and R. M. Santella describes the measurement of DNA adducts by means of detecting a fluorescent signal by a single piece of optical fibre with antibodies placed in a pocket at the end of the fibre. The device uses laser light to excite and detect the fluorescent signal. The measurement of adducts requires the preparation of a sample by its hydrolysis in order to achieve the required sensitivity.

Likewise, the device and the measurement method presented in the document Biosensors and Bioelectronics 2007, Chemiluminescent optical fiber immunosensor for detection of autoantibodies to ovarian and breast cancer-associated antigens. Orly Salama, Sebastien Herrmann, Alina Tziknovsky b, Benjamin Piura, Michael Meirovich, Ilya Trakht, Brent Reed, Leslie I. Lobel, Robert S. Marks requires the use of a label (tag, marker), e.g. chemiluminescent, and secondary antibodies for detection. The device is prepared to perform the measurement in a solution.

The document Nature Biotechnology 2000, Antibody-based nanoprobe for measurement of and fluorescent analyte in and single cell, Tuan Vo-Dinh, Jean-Pierre Alarie, Brian M. Cullum, and Guy D. Griffin describes another device using an optical fibre coated with antibodies, suitable for use in a single cell. However, in this device the measurement is also based on the detection of a fluorescent signal, and the device comprises a single piece of optical fibre connected to a fluorescence microscope.

In state of the art, some solutions allowing resignation from using labels during detection have already been indicated. The document Scientific Reports 2014, Nanoscale Label-free Bioprobes to Detect Intracellular Proteins in Single Living Cells, Wooyoung Hong, Feng Liang, Diane Schaak, Marko Loncar and Qimin Quan describes a device using an optical fibre coated with antibodies, not requiring the use of fluorescent labels, and based on the technique of surface plasmon resonance. The device has been adapted to perform a measurement in a single cell and it comprises a piece of optical fibre ended with a gold nanotube covered with antibodies. The addition of an analyte causes a shift in the LSPR signal. Likewise, the document Biosensors and Bioelectronics 2014, An enhanced LSPR fiber-optic nanoprobe for ultrasensitive detection of protein biomarkers, Mollye Sanders, Yongbin Lin, Jianjun Wei, Taylor Bono, Robert G. Lindquist describes an analogical solution, also based on an optical fibre probe and the use of an LSPR signal from a gold nanodisc coated with antibodies at the end of the probe. The device is adapted to measuring the analyte in a solution. No teaching enabling the performance of the measurement directly in the tissue have been described.

Currently known solutions do not offer a possibility of a simple, minimally invasive determination of analytes directly in tissues, including in solid tissues, e.g. but not exclusively in a solid tumour, isolated or in situ directly in the patient's body, without the necessity of using any labels and without the preceding preparation of tissues. Current diagnostic solutions require the collection of samples, preservation and/or processing, whereby they do not reflect the actual condition of the tissue. Additionally, devices using the flow of the studied substance through the device (like in the case of microplates) require considerable amounts of the sample. The use of a microprobe used for an in situ measurement ensures the safety of use and limits the amount of material necessary for determination.

BRIEF SUMMARY OF THE INVENTION

Therefore, the present inventors have developed a modification of a device enabling the detection and/or determination of the concentration of substances present in tissues in their natural state and place. The device according to the invention enables measurement in vivo or in an isolated tissue, also in a solid tissue, without any necessity of its preparation.

The used measurement method is quick and sensitive, not requiring the use of fluorescent or chemiluminescent labels (tags).

The modified device is an optical sensor using selective interaction of the studied substance with the binding agents immobilised on the surface of an optical fibre constituting an interferometer arm, wherein the optical fibre, comprising the immobilised binding agent, constituting the interferometer arm being mounted inside the guide, preferably a metal guide, enabling puncturing the tissue and a direct measurement of a substance present in the tissue, enabling its detection and/or determination of the concentration. Due to such a construction of the device according to the invention, it is possible to utilize a sensor based on the optical fibre, enabling the introduction of the sensor in a manner not disrupting the measurement and not damaging the sensor, directly into the tissue. The device according to the invention also enables an in situ measurement using a probe based on the optical fibre in a manner which is safe and minimally invasive for the patient. The guide also allows protecting the patient against a fragment of the optical fibre sensor being left in the tissue, e.g. in the case of possible fracturing or breaking of the sensor. The optical fibre can be mounted in the guide and thus shielded in part or in its whole length, which enables reducing the impact of possible shocks (movements) on the result of the measurement.

The sensor prepared according to the invention and used in the method according to the invention is an interferometer. The interferometer in the device according to the invention is placed in a guide, preferably metal, with a length ranging from approximately 0.5 to 30 cm, internal diameter, e.g. from approximately 0.1 mm to approximately 5 mm, external diameter, e.g. from approximately 0.2 to 7 mm and a shape, e.g. resembling a biopsy needle. The interferometer is attached to the input end of the guide in any suitable manner allowing the sterilisation of the sensor, e.g. with a specialised epoxy glue. Such a method of attachment ensures free inflow of the studied substance, and at the same time ensures keeping the optical fibre sensor at a distance from the guide walls, so that the movement of the guide does not affect the performed measurement and does not cause a disruption in the measurement. The method of attachment provides a barrier against the penetration of biological and chemical contaminants and substances which could disrupt the measurement.

The combination of the interferometer with the guide was accomplished in such a manner that the interferometer was placed centrally inside the guide, so that the axis of the interferometer core would not be shifted relative to the guide axis by a value higher than 100 μm (micrometres). Subsequently, the space between the interferometer and the guide was filled with e.g. epoxy glue and subjected to heating in a temperature range between +50° C. and +200° C. until achieving complete setting of the glue. The cooling of the interferometer combined with the guide was conducted in a controlled manner, i.e. the temperature drop is no faster than 10° C./s. Controlling the rate of cooling the interferometer combined with the guide allowed obtaining a loss in the optical power/attenuation of the interferometer at a level below 0.02 dB.

Therefore, the object of the invention is a device for detecting and/or determining the concentration of an analyte present in the tissue, comprising a sensor which is an optical fibre interferometer, one interferometer arm being coated with an immobilised binding agent enabling selective binding of the analyte present in the tissue, wherein said interferometer arm coated with an immobilised binding agent is mounted inside a guide enabling puncturing the tissue and performing an in situ measurement without the necessity to collect or prepare a sample, the guide being provided with a closed guide face, longitudinal perforations on the sidewalls enabling the analyte to reach the binding agent, and an opening in the input guide end for introducing the interferometer with the arm coated with the binding agent into the guide, at the input end of the guide, the opening being sealed, enabling the isolation of the interior of the guide from the surroundings, and the interferometer being mounted in a position, in which the interferometer does not touch the inside walls of the guide.

In a preferred embodiment of the device according to the invention, the interferometer is mounted centrally inside the guide, so that the axis of the interferometer core is not shifted relative to the guide axis by a value higher than 100 μm.

In a preferred embodiment of the device according to the invention, the interferometer is mounted in the guide by means of epoxy glue.

In a preferred embodiment of the device according to the invention, the interferometer is mounted in the guide by means of epoxy glue, the setting of the epoxy glue having been achieved by heating, upon which the cooling of the interferometer combined with the guide has been conducted in a controlled manner, so that the temperature drop would not exceed 10° C./s.

In a preferred embodiment of the device according to the invention, at least one interferometer arm has a length different from the remaining interferometer arms, wherein this difference in length ($\Delta L$) falls within a range from 5 to 100 μm.

In a preferred embodiment of the device according to the invention, the guide has a length from a range of 0.5-30 cm, an internal diameter of 0.1 mm-5 mm, an external diameter of, e.g. 0.2-7 mm and a shape resembling a biopsy needle. Such a preferred shape of the guide enables puncturing even hard tissues.

In a preferred embodiment of the device according to the invention, the binding agent are antibodies, their antigen binding fragments, or antigen binding affibodies.

In a particularly preferred embodiment of the device according to the invention, antibodies, their antigen binding fragments or antigen binding affibodies are antibodies, their antigen binding fragments or antigen binding affibodies for an HER2, PSA, AFP, CA19-9, CA125 or CEA antigen, respectively.

In a preferred embodiment of the device according to the invention, the analyte, is a tumour marker or another disease marker, which can be used in diagnostics of diseases or monitoring of treatment.

In a particularly preferred embodiment of the device according to the invention, the analyte is an HER2, PSA, AFP, CA19-9, CA125 or CEA tumour marker.

In an another preferred embodiment of the device according to the invention, the binding agent is a nucleic acid.

The object of the invention is also a method of detection and/or quantitative determination of an analyte present in a tissue, which comprises a step of analysing the presence and/or concentration of said substance by means of an interferometer in the device according to the invention.

In a preferred embodiment of the method according to the invention, the step of analysing the presence and/or amount of said analyte is preceded by a step of isolating the sample tissue and a step of puncturing the collected sample using the device according to the invention.

The object of the invention is also a use of the device according to the invention for detecting and/or determining the amount of an analyte present in a tissue.

In an embodiment of the use for detecting and/or determining the amount of an analyte present in a tissue according to the invention, detecting and/or determining the amount of the analyte is performed in an isolated sample tissue.

In an embodiment of the use for detecting and/or determining the amount of an analyte present in a tissue according to the invention, the analyte is a tumour marker or another disease marker which can be used in diagnostics of diseases or monitoring of treatment.

In an embodiment of the use for detecting and/or determining the amount of an analyte present in a tissue according to the invention, the analyte is an HER2, PSA, AFP, CA19-9, CA125 or CEA tumour marker.

Longitudinal perforations on the sidewalls of the guide in the device according to the invention should have a size smaller than the predicted sizes of possible splinters (shards) in the case of damaging and fracturing or breaking off a fragment of the optical fibre. Therefore, the optimal size will depend on the material from which the optical fibre is made. Determining the optimum size of the perforation falls within the scope of the abilities of a person skilled in the art.

In the described preferred embodiment, in which at least one interferometer arm has a length different from the remaining interferometer arms, this difference in length ($\Delta L$) falling within a range between 5 and 100 µm, said at least one interferometer arm whose end is coated with the binding agent or their fragments binding the antigen, can be both longer and shorter than the remaining arm (the remaining arms) of the interferometer. The presence of a difference in length falling within the above-mentioned range is significant for this particularly preferred embodiment.

In the device for detecting an analyte using an optical fibre interferometer, a particularly preferred effect is achieved by employing a suitable imbalance between the interferometer arms, which allows detecting changes corresponding to the binding of the analyte with the binding agents, e.g. antigens with antibodies with a layer thickness level of even as small as 10 nm.

Figure 1:
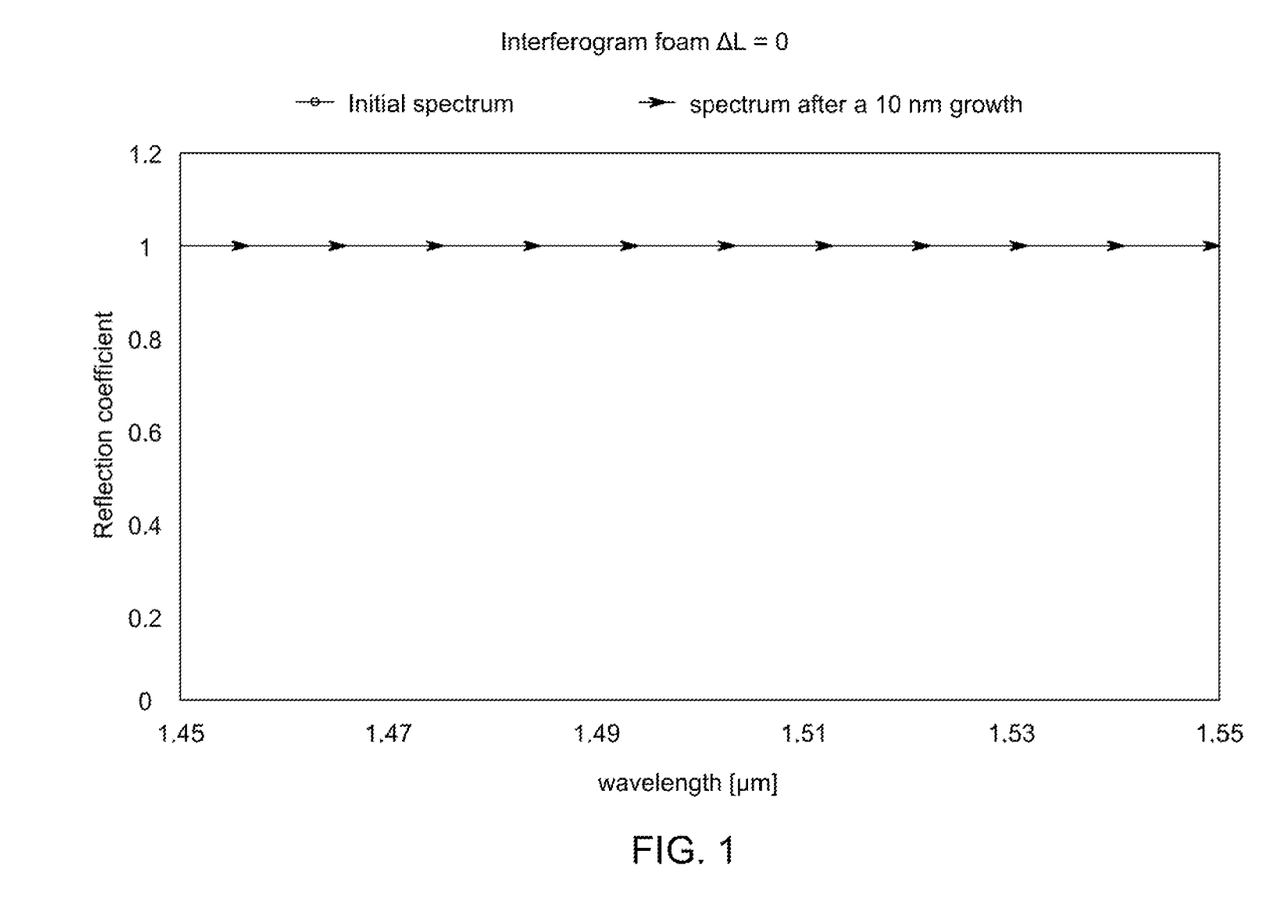
FIG. 1 presents an interferogram for the case of an interferometer known in state of the art with equal arms and a change in this interferogram upon binding with an antigen layer 10 nm in thickness.

In the case of using an optical fibre interferometer with equal arms, the detection of changes amounting to a layer thickness of 10 nm is impossible. FIG. 1 presents an interferogram for the case of an interferometer with equal arms and a change in this interferogram upon binding with an analyte layer 10 nm in thickness.

Figure 2:
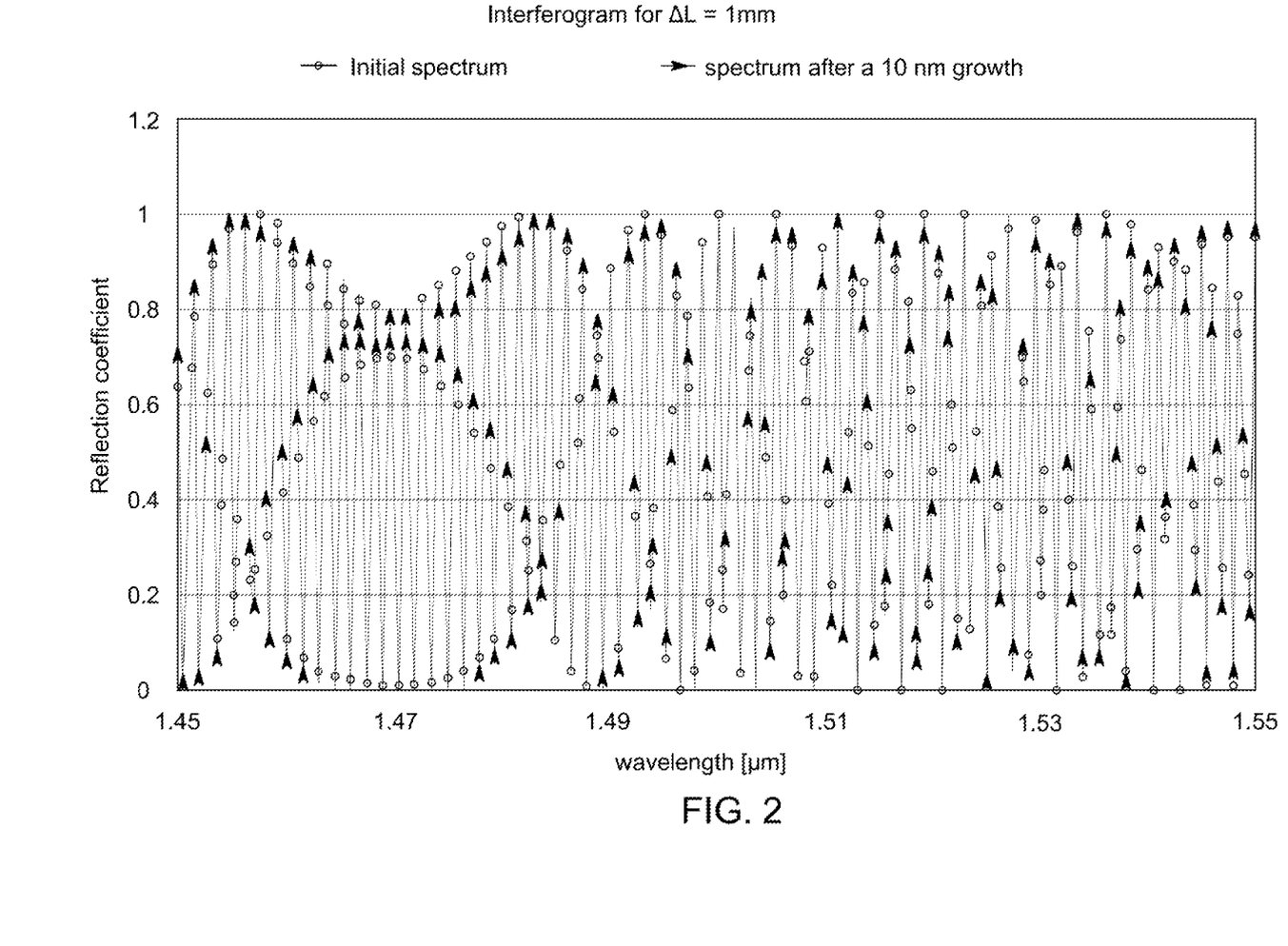
FIG. 2 presents an interferogram for the case of an interferometer with an imbalance of arms $\Delta L=1$ mm and a change in this interferogram upon binding with an antigen layer 10 nm in thickness.

On the other hand, introducing too great an imbalance (e.g. $\Delta L=1$ mm) is also disadvantageous, since the interferogram (FIG. 2) observed at the outlet does not allow a clear identification of the spectral shift corresponding to binding with a layer of the studied analyte of approximately 10 nm in thickness.

Only a suitably selected imbalance ($\Delta L$) enables the device to be adapted to detect the bound analyte, namely the binding of nanometer-scale layers. It is then possible to perform a sensitive and precise measurement for the optic fibre bound layer thickness falling within a range of approximately 1-50 nm.

Figure 3:
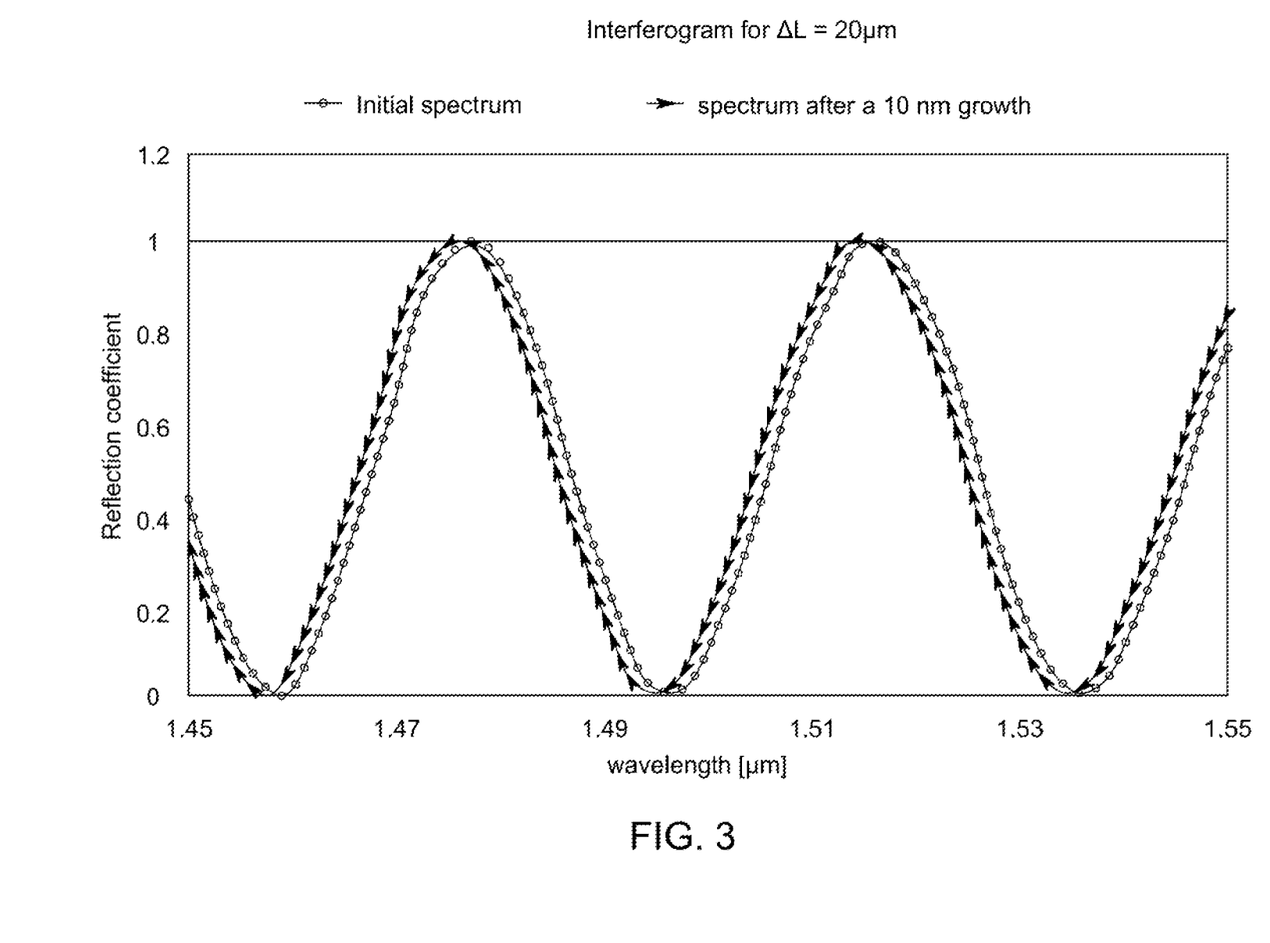
FIG. 3 presents an interferogram for an imbalance of $\Delta L=20$ μm and a comparison of the spectrum before and after binding with an antigen layer 10 nm in thickness.

FIG. 3 presents a chart for an imbalance of $\Delta L=20$ µm and a comparison of the spectrum before and after binding with an analyte layer 10 nm in thickness.

Said preferred optical fibre sensor for detection and/or quantitative determination of an analyte for use in a device according to the invention comprises a light source, a detector and a coupler, the light source, the detector and the coupler being able to be possibly connected to a circulator, the signal behind the coupler being split into at least two optical fibres—interferometer arms, at least one arm being coated with a binding agent capable of binding the analyte, and wherein the light signal:

(i) reflects from the faces of the interferometer arms, upon which the signal is directed through the coupler and possibly through the circulator into the detector, Or (ii) enters the optical power splitter maintaining the polarity, and subsequently the detector which is an optical spectrum analyser, wherein at least one of the interferometer arms has a length different from the remaining interferometer arms, and wherein this length difference ($\Delta L$) falls within a range between 5 and 35 100 µm, for example is 10 µm or 38.9 µm or 100 µm.

A particularly preferred optical fibre sensor for detection and/or quantitative determination of an analyte for use in the device according to the invention comprises a light source, a detector and a coupler, the light source, the detector and the coupler being able to be possibly connected to a circulator, the signal behind the coupler being split into at least two optical fibres—interferometer arms, and wherein the light signal reflecting from the faces of the interferometer arms, at least one interferometer arm being coated with a binding agent capable of binding the analyte, upon which the signal is directed through the coupler, and possibly through the circulator, into the detector, and wherein at least one of the interferometer arms having a length different from the remaining interferometer arms, and wherein this length difference ($\Delta L$) falls within a range between 5 and 100 µm, for example is 10 µm or 38.9 µm or 100 µm.

The method for detecting an analyte in the sample, using an optical fibre sensor provided with a light source, a coupler and a detector as well as interferometer arms, at least one of which is coated with a binding agent which is capable of binding the analyte, can for example comprise steps of:

a) emitting a light signal from the light source;
b) detecting the light waves reflected from the faces of the interferometer arms or propagating through the interferometer arms;
c) detecting a first interference pattern for the reflected or propagating light waves;
d) contacting the sample with at least one interferometer arm coated with the binding agent;
e) emitting a light signal from the light source;
f) detecting the light waves reflected from the faces of the interferometer arms or propagating through the interferometer arms;
g) detecting a second interference pattern for reflected or propagating light waves;
h) recording the presence of the analyte in the studied sample in the case of detecting a 25 spectral shift between the first and the second interference patterns.

Additionally, the following step can be present:

i) determining the amount of the analyte, in the sample based on the size of the shift between the first and the second interference patterns. In a preferred embodiment of the device according to the invention, the guide is made of metal.

The binding agents used in the device according to the invention can be proteins, preferably antibodies or their analogues. The antibodies used in the method according to the invention can be any antibodies enabling the detection of an antigen. The antibodies can for example be immunoglobulins G, e.g. IgG from rabbit serum. These can be, e.g. monoclonal and polyclonal antibodies, human, animal, chimeric, humanized, bispecific or belonging to any other group of antibodies known to a person skilled in the art. In the method according to the invention, an antigen binding fragment of the antibody can also be used, which is any of its fragments which maintain the ability to bind the antigen. Such fragments are known to a person skilled in the art and comprise, e.g. Fab, F(ab')2 or scFv fragments and others.

The used analogue of an antibody can also be an affibody. Within the meaning of the present description, the term "affibody" means a recombined protein comprised of one polypeptide chain, comprising a domain responsible for selective interaction with an antigen, e.g. an HER2 tumour marker, which can be bound with another protein ensuring better properties for binding with the antigen, higher stability and additional functions, e.g. the possibility to controllably bind with another substance or a solid surface. Its mass usually falls within a range between several and over a dozen kilodaltons.

Antibodies are used commonly in the diagnostic of tumours, e.g. in the immunohistochemical method for staining tissue sections, and affibodies are analogues of antibodies, retaining the properties of binding with specific antigens, but having sizes considerably e.g. 10 times smaller. Due to this, they are more resistant to physical and biological factors, e.g. temperature, strict binding conditions with the optical fibre (chemical reagents) and degradation by proteolytic enzymes during penetration of the tissue. These properties cause the coating of the optical fibre, covered with particles such as affibodies, to be more stable with respect to the activity of binding the specific antigen, e.g. tumour markers. Additionally, a directed immobilisation of substances at the surface of the optical fibre is preferably possible due to a cysteine moiety introduced at the end of the affibody. This ensures higher activity and maintaining the specificity for the marker measured in the tissue.

In another embodiment, the binding agent can be nucleic acids, e.g. DNA.

The binding agents can be immobilised in various manners known in the art. Preferably, the binding agents are covalently bound with the surface of the optical fibre.

The analytes determined in the tissue can be various substances, detecting and/or determining the concentration of which is desirable. In a preferred embodiment, substances determined in the tissue can be tumour markers, e.g. HER2, PSA, AFP, CA19-9, CA125, CEA or other markers known in the art which can be used in diagnostic of diseases or monitoring of treatment.

The device according to the invention can be used to perform measurements ex vivo or in situ in an individual. The individual can be an animal, preferably a mammal, most preferably a human.

Coating with antibodies or their antigen binding fragments can be performed in various manners. An exemplary, not limiting the scope of the invention, process of coating a piece of optical fibre with antibodies or their antigen binding fragments can be conducted according to the method presented below.

The coated end of the optical fibre is submerged in an alkaline solution and subsequently rinsed in demineralized water and dried. It is then kept for 10-30 min. at a high temperature in an acidic solution of silane. Subsequently, the tip (end) of the optical fibre is rinsed, dried, and subsequently submerged in a solution of the coupling agent, upon which it is again rinsed and incubated with a solution comprising antibodies or their antigen binding fragments. The optical fibre prepared in such a manner is stored chilled.

In a more particular, nonlimiting embodiment, the coated end of the optical fibre is submerged in a solution of NaOH with a concentration between 1 M and 1.3 M for a time of 5 min. to 10 min., and subsequently rinsed with purified water and dried in the air for approximately 15 min.

It is then kept for approximately 3 hours in a temperature of approximately 90° C. in a 10% solution of (3-glycidyloxypropyl)trimethoxysilane (GOPS) with water (volume fraction) with pH=2 to pH=2.5, adjusted by means of, e.g. a 1 M solution of HCl. Subsequently, the tip of the optical fibre is rinsed in ethanol, upon which it is dried for 10 h to 13 h in a temperature of approximately 105° C. in vacuum or in an argon atmosphere. Subsequently, it is submerged in a 15 100 mg/ml solution of 1,1'-carbonyldiimidazole (CDI) in acetonitrile (ACN) for approximately 20 min., upon which it is rinsed with acetonitrile and a solution of phosphate buffer (PBS) and incubated in a 1.2 mg/ml solution of PBS comprising antibodies, e.g. immunoglobulins G from rabbit serum for 4 days in a temperature of approximately 4° C. or for 1-2 days in room temperature, upon which it is stored in a solution of PBS for 12 h in a temperature of 4° C. The optical fibre prepared in such a manner is properly secured and stored in a temperature of 4° C. with its tip submerged in a PBS solution.

The advantages of such a coating method are: maintaining the activity of antibodies or their antigen binding fragments at a level above 95%, a large number of bound antibodies or their antigen binding fragments, relatively low material costs and the possibility to easily scale up the production.

The process of coating a piece of optical fibre with antibodies or their antigen binding fragments can also be conducted using alternative methods. For example, after degreasing, the optical fibre is submerged in distilled water and boiled. Upon removal from water, it is placed in a solution of silane. Subsequently, the optical fibre is rinsed in a solvent, and subsequently submerged in a solution of the coupling agent. Upon rinsing, the optical fibre is placed in a solution of antibodies or their antigen binding fragments.

In a more particular, nonlimiting embodiment, the optical fibre is first degreased by means of isopropyl alcohol in order to remove contaminants. Subsequently, the optical fibre is submerged in distilled water and boiled for approximately 10-20 minutes. Upon removal from water, the optical fibre is placed in a 1-3% solution of (3-mercaptopropyl)trimethoxysilane (MPTS) in toluene. After 20-45 minutes, the optical fibre is removed and rinsed in toluene, and subsequently submerged in a solution of N-succinimidyl 4-maleimido-butyrate (GMBS) with a concentration of 4-8 mg/10 ml of ethanol with a concentration of 96%. The optical fibre is kept in this solution for 60-90 minutes. It is subsequently rinsed once in ethanol and three times in distilled water. The optical fibre is later placed in a solution of antibodies with a concentration of 0.2-1 mg/ml in a solution of phosphate buffer. The coated optical fibre is removed from the solution after 12-18 hours and rinsed in distilled water.

Therefore, the invention provides a possibility of measuring biologically important particles in a manner which is direct, without the use of labels, immediate (taking place in real time), without the necessity to prepare the tissue, and minimally invasive due to the size of the used sensor (preferably approximately 0.1-50 microns in diameter). Due to the covalent binding of antibodies or their derivatives (affibodies), their release into the body is minimised, which increases the clinical potential of such a device.

The device according to the invention comprises an optical fibre sensor, being a specially prepared interferometer, a light source and a detector. The sensor is prepared by immobilisation of the binding agent on the surface of a piece of optical fibre, for example, in a preferred embodiment, a protein substance capable of specific interaction with a tumour marker. The amount of the determined substance bound with the interferometer (e.g. in a preferred embodiment a tumour marker) is measured as a spectral shift.

The magnitude of the spectral shift is determined by means of a standard substance with a known concentration and the given value of the shift is attributed to a specific amount of the marker.

DETAILED DESCRIPTION OF THE INVENTION

Examples

Example 1. A Sensor for Detecting an Analyte

Example 1A

Figure 4:
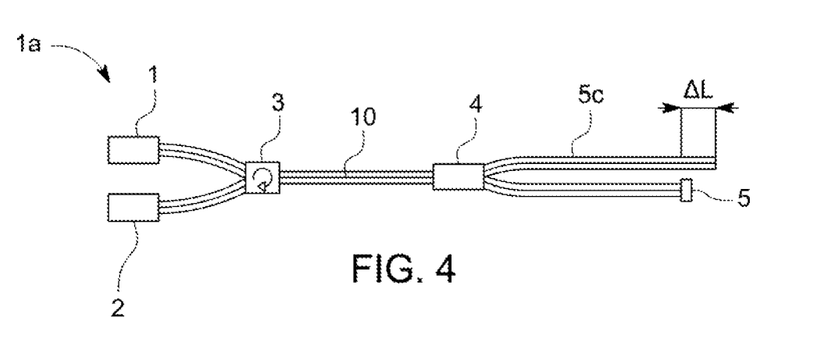
FIG. 4 presents an embodiment of an optical fibre sensor for detecting the analyte.

In a preferred embodiment presented in FIG. 4, a sensor 1a for detecting an analyte comprises a light source 1, a detector 2 and a coupler 4 connected to a circulator 3. The light source 1, in this particular case, is a superluminescent diode SLED 1550 nm Exalos number EXS210048-02, and the detector 2, in this particular case, is an optical spectrum analyser OSA ANDO AQ- 6315B. A Corning SMF-28e+ optical fibre and an FBT 50:50 coupler produced by Fibrain were used.

The signal from the light source 1 is delivered to the circulator 3, from which it is subsequently delivered to the coupler 4 by single-mode pieces of optical fibre. The signal behind the coupler 4 is split into two optical fibers-interferometer arms (optical fiber arm 5 having fiber arm axis 5a, another optical fiber arm 5c). The signal is reflected from optical fiber faces, one of the arms 5 being coated with antibodies (binding agent 5b). The signal returns through the coupler 4 to the circulator 3, from which it is further led into the detector 2.

The interferometer arm whose end is not coated is longer by $\Delta L=38.9$ μm.

One of the interferometer arms is coated with antibodies, which in this particular case is immunoglobulin G (IgG) from rabbit serum. These antibodies enable the detection of an antigen, which in this particular case is anti-rabbit immunoglobulin (obtained as a result of placing rabbit IgG in goat's blood plasma and separating the antigen) tagged with a luminescent marker FITC (Anti-IgG-FITC). Interference fringes in the wavelength domain, whose shift indicates the binding of antigens with antibodies, are visible on the detector.

The process of coating a piece of optical fibre with antibodies was conducted according to the method presented below. The coated end of the optical fibre was submerged in a solution of NaOH with a concentration above 1 M for 10 min., and subsequently rinsed in purified water and dried in the air for 15 min. It was then kept for hours in a temperature of 90° C. in a 10% solution of (3-glycidyloxypropyl) trimethoxysilane (GOPS) with water (volume fraction) with pH=2, established by means of a 1 M solution of HCl. Subsequently, the tip of the optical fibre was rinsed in ethanol, upon which it was dried for 13 h in a temperature of 105° C. in vacuum or in an argon atmosphere. Subsequently, it was submerged in a 100 mg/ml solution of 1,1'-carbonyldiimidazole (CDI) in acetonitrile (ACN) for 20 min., upon which it was rinsed in acetonitrile and a solution of phosphate buffer (PBS) and incubated in a 1.2 mg/ml solution of PBS comprising the antibodies of immunoglobulin G from rabbit serum for 4 days in a temperature of 4° C., upon which it was stored in a solution of PBS for 12 h in a temperature of 4° C.

In order to perform the measurement, the device is brought into contact with the sample, so that the analyte present in the sample could be bound with the binding agent.

Figure 5:
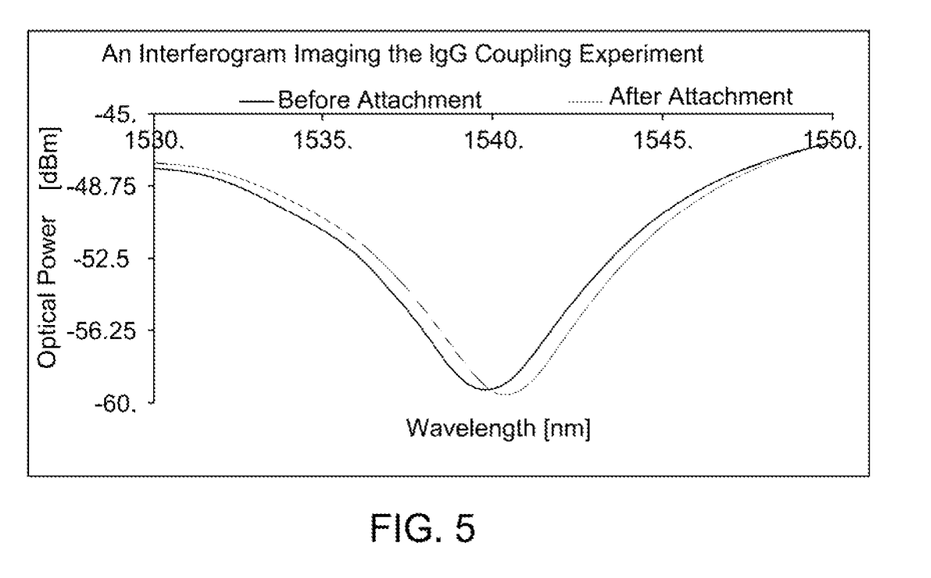
FIG. 5 presents a spectral distribution observed on the detector for the sensor of FIG. 4.

FIG. 5 presents the spectral distribution observed on the detector. The binding of antigens caused a spectral shift of 0.6 nm. In order to determine the amount of the analyte, standard solutions with known concentrations of the analyte are prepared and a calibration curve is established for the dependence of the change in the spectral shift on the amount of the analyte. The concentration of the analyte in the sample is determined by means of a calibration curve established in this manner.

Calculation of the optical thickness of layers bound in an interferometer system:

LIST OF REFERENCES $\lambda 1$—The wavelength at which a spectral minimum occurs before an increase in the thickness of the layers $\lambda 2$—The wavelength at which a spectral minimum occurs after an increase in the thickness of the layers $\phi$—Light phase for the given wavelength upon passing through the optical system Lp—Initial interferometer imbalance length np—The refractive index of the material ensuring the initial interferometer imbalance $\Delta L$—change in the length of the material at the face of the interferometer $n\Delta$—The refractive index of the material which is the increasing material The minimum before the growth (increase) of the layers is considered to be the initial light phase φ1. After the growth of the optical thickness of the layer, the same phase condition φ2 will be fulfilled for another wavelength. Such a condition can be written down as:

$$\varphi_1 = \frac{2\pi(L_p n_p)}{\lambda_1}$$

$$\varphi_2 = \frac{2\pi(L_p n_p + \Delta L(n_\Delta - 1))}{\lambda_2}$$

Assuming

φ1=φ2

We obtain $$\frac{2\pi(L_p n_p)}{\lambda_1} = \frac{2\pi(L_p n_p + \Delta L(n_\Delta - 1))}{\lambda_2}$$

Due to this, the following dependence can be reached after transformations:

$$|\Delta L| = \frac{L_p n_p \left(\frac{\lambda_2}{\lambda_1} - 1\right)}{n_\Delta - 1}$$

This dependence describes the change in the physical length of the layer which was bound in the system. More detailed explanations involving the calculation method can also be found in Hariharan, P. (2007). Basics of Interferometry. Elsevier Inc.

Example 1B

Figure 6:
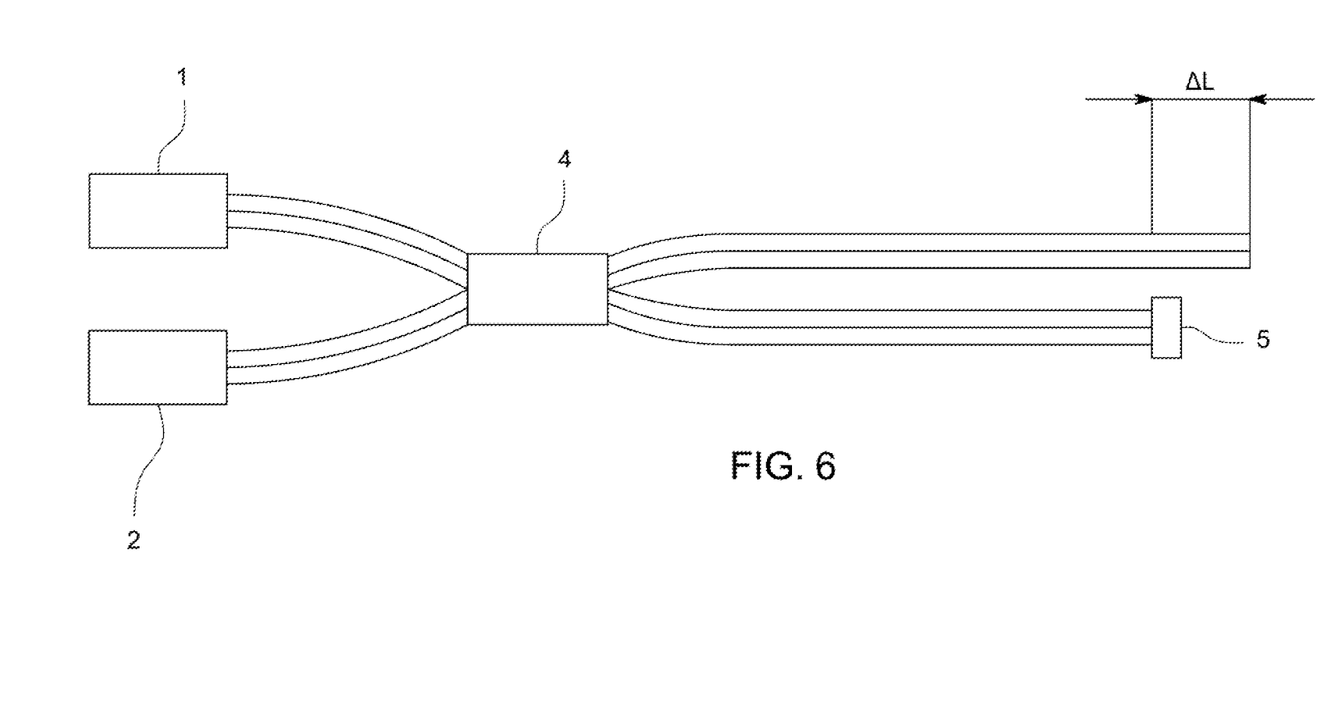
FIG. 6 presents an alternative, preferred embodiment of the optical fibre sensor for detecting the analyte.

In an alternative, preferred embodiment presented in FIG. 6, the sensor for detecting the analyte comprises a light source 1, a detector 2 and a coupler 4. The light source 1 in this particular case is a supercontinuum-type source SLED 1540 nm Yenista OSICS SLD 1550, and the detector 2 in this particular case is an OSA Yokogawa AQ6370D spectrometer. A Standard Singlemode Fibre (SSMF) optical fibre fulfilling the guidelines of ITU-T, G.652 from the Draka company and a 10202A-50 coupler from the Thorlabs company were used.

The signal from the light source 1 is delivered to the coupler 4 via optical fibres. The signal behind the coupler 4 is split into two optical fibres—interferometer arms. The signal is reflected from the optical fibre faces, one of the arms 5 being coated with antibodies. The signal returns through the coupler 4 to the detector 2.

The interferometer arm whose end is coated is longer by ΔL=10 µm.

One of the interferometer arms is coated with antibodies, which in this particular case is immunoglobulin G (IgG) from rabbit serum. These antibodies enable the detection of an antigen, which in this particular case is anti-rabbit immunoglobulin (obtained as a result of placing rabbit IgG in goat's blood plasma and separating the antigen) tagged with a luminescent marker FITC (Anti-IgG-FITC). Interference fringes in the wavelength domain, whose shift indicates the binding of antigens with antibodies, are visible on the detector.

The process of covering one of the interferometer arms with antibodies consisted of several steps. The optical fibre was first degreased by means of isopropyl alcohol in order to remove contaminants. Subsequently, the optical fibre was submerged in distilled water and boiled for 15 minutes. Upon removal from water, the optical fibre was placed in a 2% solution of (3-mercaptopropyl)trimethoxysilane (MPTS) in toluene. After 30 minutes the optical fibre was removed and rinsed in toluene, and subsequently submerged in a solution of N-succinimidyl 4-20 maleimido-butyrate (GMBS, no. CAS 8-307-12-6) with a concentration of 6 mg/10 ml of ethanol with a concentration of 96%. The optical fibre was kept in this solution for 60 minutes. It was subsequently rinsed once in ethanol and three times in distilled water. The optical fibre was later placed in a solution of antibodies with a concentration of 1 mg/ml in a solution of phosphate buffer. The coated optical fibre was removed from the solution after 12 hours and rinsed in distilled water.

Figure 7:
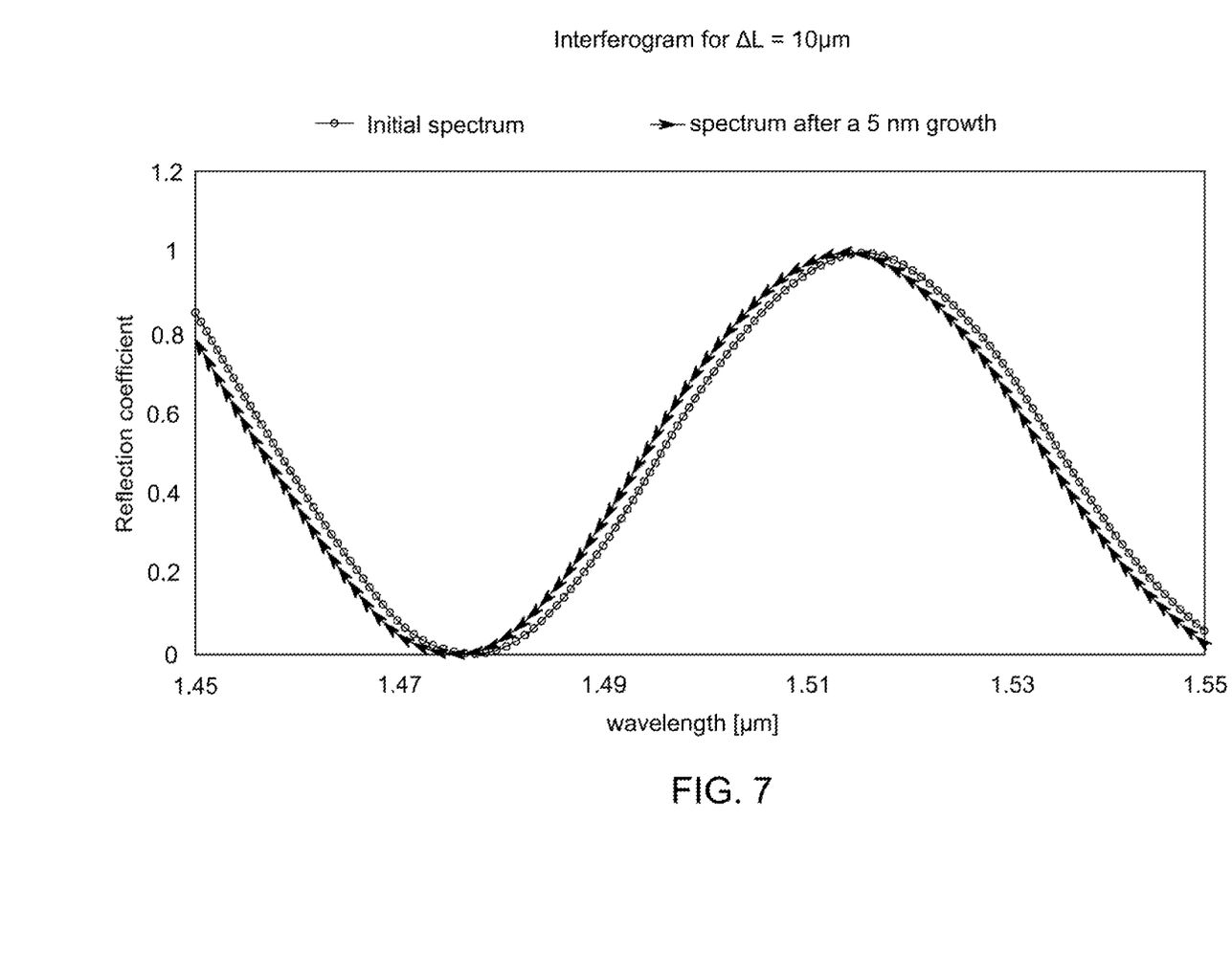
FIG. 7 presents a spectral distribution observed on the detector for the sensor of FIG. 6.

FIG. 7 presents the spectral distribution observed on the detector. The binding of antigens caused a spectral shift of 0.5 nm. In order to determine the amount of the analyte, standard solutions with known concentrations of the analyte are prepared and a calibration curve is established for the dependence of the change in the spectral shift on the amount of the analyte. The concentration of the analyte in the sample is determined by means of the calibration curve established in this manner. The method for calculating the thickness of the layer of the bound analyte is such as in Example 1A.

Example 1C

Figure 8:
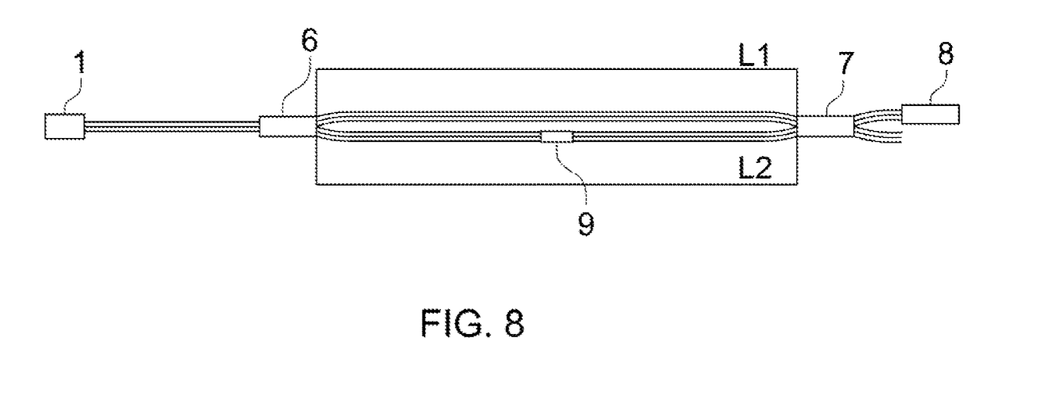
FIG. 8 presents an alternative, preferred embodiment of the optical fibre sensor for detecting the analyte.

In a preferred embodiment presented in FIG. 8, the device for detecting the analyte comprises a superluminescent diode 1 (S5FC1018S—SM Benchtop SLD Source) emitting a polarised light with a central spectral wavelength of 1310 nm and a spectral half-width of 50 nm, connected to a PANDA-type single-mode at a wavelength of 1260 nm or more optical fibre maintaining the polarity (PM1300-XP from the Thorlabs company), a PLC-type optical power splitter 6 with an optical power division of 50%:50% for a wavelength of 1310 nm, two PANDA-type single-mode at a wavelength of 1260 nm and more optical fibres maintaining the polarity with lengths of L1=50 mm, L2=50 mm, one of which comprises in the middle of its length a break 9, an optical power splitter 7 maintaining the polarity and an optical spectrum analyser 8. A PMC1310-50B-FC coupler from the Thorlabs company was used.

The signal from the light source 1 is delivered to the splitter 6. The signal behind the splitter 6 is split into two optical fibres—interferometer arms. The signal propagates through the interferometer arms, whose different lengths ensure the initial imbalance of the interferometer. One of the optical fibres comprises a break 9 in the middle of its length, and the ends on both sides of the break 9 are placed at a distance of 0.1 mm from each other. Through the coupler 7 the signal enters the optical spectrum analyser 8.

One of the tips of the cut optical fibre is coated with antibodies like in Example 1A, which in this particular case is immunoglobulin G (IgG) from rabbit serum. These antibodies enable the detection of an antigen, which in this particular case is anti-rabbit immunoglobulin (obtained as a result of placing rabbit IgG in goat's blood plasma and separating the antigen) tagged with a luminescent marker FITC (Anti-IgG-FITC). The coated end of the optical fibre has been moved back to the second tip at the same distance as before.

The measurement is performed by contacting the coated end of the optical fibre with the studied sample, so that the analyte could by bound by the binding agent.

Figure 9:
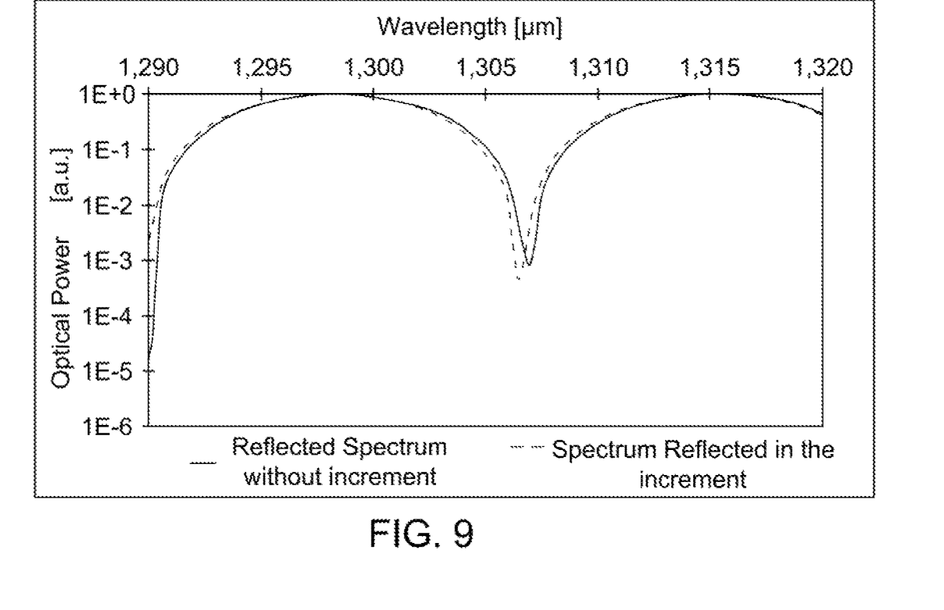
FIG. 9 presents a spectral distribution observed on the detector for the sensor of FIG. 8.

Interference fringes in the wavelength domain, whose shift by 0.5 nm indicates the binding of an antigen layer with a thickness of 115 nm with antibodies, are visible on the detector (FIG. 9). In order to determine the amount of the analyte, standard solutions with known concentrations of the analyte are prepared and a calibration curve is established for the dependence of the change in the spectral shift on the amount of the analyte. The concentration of the analyte in the sample is determined by means of the calibration curve established in this manner. The method for calculating the thickness of the layer of the bound analyte is such as in Example 1A.

Example 1D. Coating with Affibodies

In a preferred embodiment presented in FIG. 4, the device for detecting the analyte comprises a light source 1, a detector 2 and a coupler 4 connected to a circulator 3. The light source 1 in this particular case is a superluminescent diode SLED 1550 nm Exalos number EXS210048-02, and the detector 2 in this particular case is an optical spectrum analyser OSA ANDO AQ-6315B. A Corning SMF-28e+ optical fibre and an FBT 50:50 coupler produced by Fibrain were used.

The signal from the light source 1 is delivered to the circulator 3, from which it is subsequently delivered to the coupler 4 by single-mode pieces of optical fibre. The signal behind the coupler 4 is split into two optical fibres—interferometer arms. The signal is reflected from the optical fibre faces, one of the arms 5 being coated with affibodies. The signal returns through the coupler 4 5 to the circulator 3, from which it is further led into the detector 2.

The interferometer arm whose end is not coated is longer by $\Delta L=38.9$ μm.

In the case of the affibodies, immobilisation by means of thiol groups is applied using the available reagents (Thermofisher Scientific, Waltham, Mass.). To this end, the end of the interferometer is submerged in 1 M sulphuric acid for 1 h and subsequently rinsed with distilled water and submerged for 15 min in ethanol and for another 15 min in acetone. The cleaned end of the optical fibre is subsequently submerged in anhydrous acetone comprising 2% of APTES (3-aminopropyltriethoxysilane) for 0.5-5 min. Upon the end of the reaction, the optical fibre is rinsed in anhydrous acetone and dried in the air for 15-30 min. Subsequently, the optical fibre is incubated in a cross-linking buffer (50 mM of sodium phosphate, 0.15 M of NaCl, 10 mM of EDTA, pH 7.2) comprising 2 mg/ml of Sulfo-SMCC (sulphosuccinimidyl 4-(N-maleimidomethyl)cyclohexane-1-carboxylate) for 1 h in room temperature. After rinsing in the cross-linking buffer and drying in the air for 30 min., the optical fibre is stored in 4° C. in a dessicator until the moment of incubation with the affibody.

In order to reduce the terminal thiol groups, to a solution of affibody with a concentration of 1 mg/ml in a reducing buffer (50 mM of sodium phosphate, 150 mM of NaCl, 2 mM of EDTA, pH 7.5), DTT (dithiothreitol) is added to obtain the final concentration of 20 mM with a subsequent incubation for 1-2 hours in room temperature or for 45 min in 37° C. The surplus of DTT should be removed by column filtration, e.g. with Sephadex G-25, equilibrated with the cross-linking buffer. The collected eluent comprising the affibody with a reduced thiol group should be immediately used to modify the previously prepared optical fibre. To this end, the end of the optical fibre is incubated in a solution of the Affibody for 2-4 h in room temperature and subsequently rinsed by means of the cross-linking buffer and stored in a solution of physiological saline (PBS) in 4° C.

Example 2. The Device for Performing Measurements Directly in Tissue

The interferometer according to Example 1A or 1B or 1C or 1D is placed in a metal guide 30 with a length ranging between 0.5 and 30 cm, an internal diameter of 0.1 mm-5 mm, an external diameter of 0.2-7 mm and a shape resembling a biopsy needle. The interferometer 10 is introduced through the opening 32 in the input end 34 of the guide and is attached to the input end 34 of the guide 30 by specialised epoxy glue, e.g. MULTIBOND-1101 from the MULTIBOND company, so that the surface of the interferometer does not touch the walls of the guide (like in FIG. 10). The joining of the interferometer with the guide was accomplished in such a manner that the interferometer was placed centrally inside the guide, so that the axis of the interferometer core would not be shifted relative to the guide axis by a value higher than 100 μm (micrometres). Subsequently, the space between the interferometer and the guide was filled with epoxy glue and subjected to heating in a temperature range between +50° C. and +200° C. until achieving complete setting of the glue. Cooling the interferometer combined with the guide was conducted in a controlled manner, i.e. the temperature drop was no faster than 10° C./s. Controlling the rate of cooling the interferometer combined with the guide allowed obtaining a loss in the optical power/attenuation of the interferometer at a level below 0.02 dB.

Tests presenting the impact of sealing on attenuation/loss have been performed. The used measurement equipment:

A set for the measurement and monitoring of the changes in insertion loss (insertion attenuation):

The measurements used a device from the EXFO-IQ203 company integrated in a panel form, provided with:

a laser source (IQ2123 ORL) with two wavelengths: 1310 nm+20/−25 nm and 1550 nm+10/−40 nm, with a spectral width of 45/65 nm (1310/1550 nm), with a temperature stability of 0.03 dB (t=8 h T=0 . . . 50° C., and an InGaAs (IQ1103) detector measurement range 800-1700 nm, relative precision of power measurement 0.015 dB, The results of the conducted tests are presented in Table 1 below:

TABLE 1

The results of the studies of changes in insertion loss.
A IL at airtight connections performed after the test

| Sample no. | $P_{in}$ [μW] [before sealing] | $P_{out}$ [μW] [after sealing] | A IL [dB] | Test results (The change in attenuation after the test should not exceed 0.2 dB for the criteria of Telcordia GR1221) P-positive N-negative |
|---|---|---|---|---|
| 1 | 5.373 | 5.342 | 0.00 | P |
| 2 | 6.338 | 6.338 | 0.00 | P |
| 3 | 6.695 | 6.679 | 0.01 | P |
| 4 | 6.203 | 6.177 | 0.02 | P |
| 5 | 6.811 | 6.790 | 0.01 | P |
| 6 | 6.510 | 6.513 | 0.00 | P |
| 7 | 6.708 | 6.709 | 0.00 | P |

TABLE 1-continued

The results of the studies of changes in insertion loss.
A IL at airtight connections performed after the test

| Sample no. | $P_{in}$ [μW] [before sealing] | $P_{out}$ [μW] [after sealing] | A IL [dB] | Test results (The change in attenuation after the test should not exceed 0.2 dB for the criteria of Telcordia GR1221) P-positive N-negative |
|---|---|---|---|---|
| 8 | 6.614 | 6.613 | 0.00 | P |
| 9 | 6.844 | 6.834 | 0.01 | P |
| 10 | 6.371 | 6.359 | 0.01 | P |
| 11 | 5.831 | 5.827 | 0.00 | P |
| 12 | 5.750 | 5.755 | 0.00 | P |
| 13 | 6.227 | 6.231 | 0.00 | P |
| 14 | 6.285 | 6.275 | 0.01 | P |
| 15 | 6.502 | 6.488 | 0.01 | P |
| 16 | 5.968 | 5.945 | 0.02 | P |
| 17 | 6.281 | 6.285 | 0.00 | P |
| 18 | 6.330 | 6.324 | 0.00 | P |
| 19 | 6.480 | 6.451 | 0.02 | P |
| 20 | 6.524 | 6.520 | 0.00 | P |
| 21 | 6.174 | 6.173 | 0.00 | P |
| mean | | | 0.01 | |

The interferometer attached to the input end of the guide ensures the ability to sterilise the sensor and ensures free inflow of the tested substance, and at the same time ensures keeping the optical fibre sensor at a distance from the guide walls, so that the movement of the guide does not affect the performed measurement. Such a method of attachment provides a barrier against the penetration of biological and chemical contaminants and substances which could disrupt the measurement.

Figure 10:
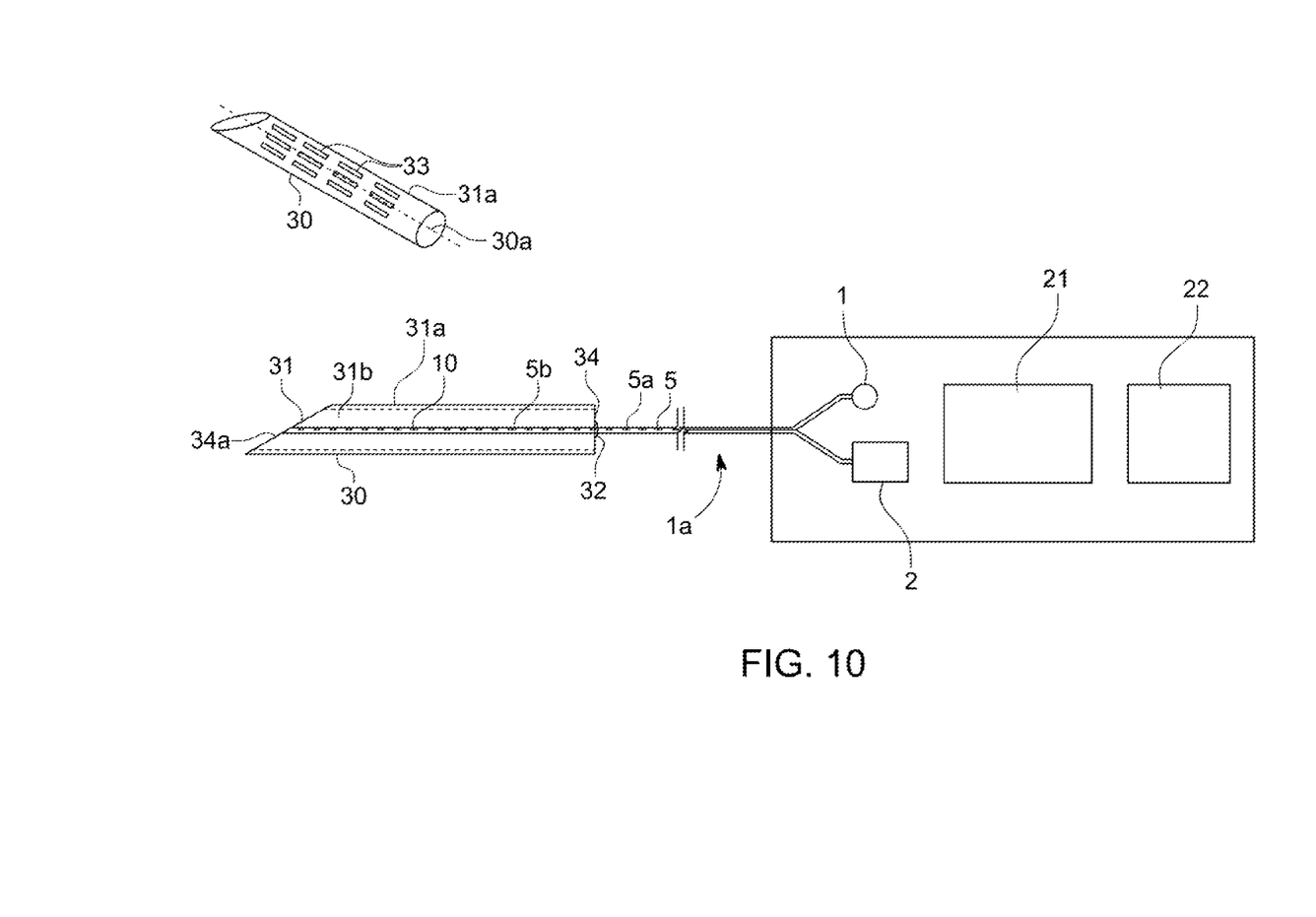
FIG. 10 presents a construction layout of the device according to an embodiment of the invention.

The guide 30 with guide axis 30a has a closed guide face 31 at a contact end 34a of the guide and longitudinal perforations 33 in sidewall 31a, enabling the analyte to reach the interferometer 10. The opening 32 in the input end 34 of the guide, constituting an entrance for the piece of optical fibre, of the interferometer 10 into the guide 30 is sealed, enabling a tight isolation of the interior 31b of the guide 30 from the surroundings.

The device in this embodiment also comprises, besides the light source 1 and the detector 2, a monitor 21 and a printer 22.

Example 3. Measurement of the Concentration of the HER2 Tumour Marker

Example 3A. Measurement with Antibodies

For the measurement of the HER2 tumour marker, a piece of optical fibre is prepared by immobilising the antibodies which selectively bind the HER2 tumour marker (anti-HER2 monoclonal antibodies, R&D Systems, Minneapolis, Minn.), as described in Example 1, the difference being that the binding agent is immunoglobulin selectively binding the HER2 tumour marker (anti-HER2 monoclonal antibodies, R&D Systems, Minneapolis, Minn.).

The measurement of the concentration of the tumour marker is performed by introducing for 5 sec.-15 min. the optical probe described in Example 1A or 1B or 1C, placed inside a metal guide, as described in Example 2, into the tissue by direct puncturing therewith the tumour tissue in the patient's body (similar as during a diagnostic biopsy performed with a biopsy needle) or directly after cutting off the tumour or by submerging it in a tissue homogenate obtained by mechanical dispersion thereof. The concentration of the marker present in the tissue corresponds to the amount of markers bound to the surface of the interferometer, and the value of the concentration is determined based on the spectral shift.

Example 3B. Measurement with Affibodies

The method for making an optical probe is different from the one from Example 3A in that instead of the antibodies, affibodies are immobilised using thiol groups, as described in Example 1D. The sensor is placed in the guide as described in Example 2. The measurement of a tumour marker, e.g. HER2, is performed similarly to Example 3A.

LIST OF REFERENCES

1—light source
2—detector
3—circulator
4—coupler
5—interferometer arm coated with a binding agent
6—optical power splitter
7—optical power splitter maintaining the polarity
8—optical spectrum analyser
9—break in the course of the optical fibre
10—interferometer
21—monitor
22—printer
30—guide
31—guide face
32—opening in the input end of the guide
33—perforations
34—input end of the guide

We claim:

1. A device for presence and concentration of an analyte present in a tissue, comprising:
   a sensor being comprised of an interferometer,
   wherein said interferometer comprises an optical fiber arm, having a fiber arm axis, and a binding agent being coated on the arm so as to enable a selective binding of an analyte present in a tissue; and
   a guide
   having an input end, a contact end opposite said input end, and a guide axis,
   wherein said guide is comprised of:
      a sidewall being between said input end and said contact end and defining an interior,
      a closed guide face at said contact end,
      a plurality of longitudinal perforations on said sidewalls so as to enable the analyte to reach said binding agent through said guide, and
      an opening at said input end, said interferometer being centrally mounted within said guide through said opening without contacting said sidewall, said fiber arm axis being coaxial with said guide axis, said opening being sealed so as to isolate said interior from surroundings except through said plurality of longitudinal perforations.

2. The device, according to claim 1, wherein said fiber arm axis is shifted relative to said guide axis by less than 100 μm.

3. The device, according to claim 1, wherein said interferometer is centrally mounted within said guide by epoxy glue.

4. The device, according to claim 3, wherein said epoxy glue is heat set to said interferometer and said guide by a temperature drop less than 10° C./s.

5. The device, according to claim 1, wherein said guide is comprised of metal.

6. The device, according to claim 1, wherein said guide has a guide length in a range of 0.5-30 cm, an internal diameter of 0.1 mm -5 mm, an external diameter of 0.2-7 mm, and a shape resembling a biopsy needle.

7. The device, according to claim 1, wherein said binding agent is comprised of at least one of a group consisting of: antibodies, antigen binding fragments, and antigen binding antibodies.

8. The device, according to claim 7, wherein said binding agent is selected for the analyte being a tumour marker or another disease marker so as to diagnose diseases or monitor treatment.

9. The device according to claim 8, wherein said binding agent is selected for the analyte being an HER2, PSA, AFP, CA19-9, CA125 or CEA tumour marker.

10. The device, according to claim 1, wherein said binding agent is comprised of a nucleic acid.

11. A method for an analyte, the method comprising the steps of:
preparing a device, according to 1,
wherein said interferometer further comprises a light source and a detector;
emitting a light signal from said light source;
detecting light waves from said optical fiber arm with said detector so as to determine a first interference pattern;
contacting a tissue with said optical fiber arm so as to bind analyte in said tissue with said binding agent;
emitting another light signal from said light source;
detecting additional light waves from said optical fiber arm so as to determine a second interference pattern;
determining a spectral shift between said first interference pattern and said second interference pattern so as to detect presence of the analyte in said tissue;
determining a size of said spectral shift so as to detect a quantitative measure of the analyte in said tissue; and
recording said presence and said quantitative measure.

12. The method, according to claim 11, wherein the step of contacting said tissue with said optical fiber arm is comprised of the step of: puncturing a sample of said tissue with said closed guide face.

13. The device, according to claim 1, said optical fiber arm having an optical fiber arm length,
wherein said interferometer further comprises another optical fiber arm, having another optical fiber arm length, and
wherein a difference between said optical fiber arm length and said another optical fiber arm length ranges from 5 to 100 μm.

* * * * *